United States Patent [19]

Gaudiana et al.

[11] Patent Number: 5,132,430
[45] Date of Patent: Jul. 21, 1992

[54] HIGH REFRACTIVE INDEX POLYMERS

[75] Inventors: Russell A. Gaudiana, Merrimack, N.H.; Richard A. Minns, Arlington; Howard G. Rogers, Weston, both of Mass.

[73] Assignee: Polaroid Corporation, Cambridge, Mass.

[21] Appl. No.: 721,191

[22] Filed: Jun. 26, 1991

[51] Int. Cl.$^5$ .......................................... C07D 209/82
[52] U.S. Cl. .................................................. 548/444
[58] Field of Search ........................................ 548/444

[56] References Cited

U.S. PATENT DOCUMENTS 4,426,505  1/1984  Minns ................................. 526/283

FOREIGN PATENT DOCUMENTS 620733  3/1949  United Kingdom ................. 548/444

OTHER PUBLICATIONS

S. H. Tucker, Iodination in the Carbazole Series, J. Chem. Soc., pp. 546-553 (1926).
D. Bailey et al., Functional Polymers. III. Endcapping and Substitution on Polymers with Compounds Containing Ultraviolet-Absorbing Groups, J. Macromol. Sci.—Chem., A12 (5) pp. 661–699 (1978).
M. Biswas et al., Recent Progress in Carbazole Based Polymers, Polymer-vol. 23, Nov., pp. 1713-1726 (1981).
C. Hu et al., Synthesis and Photoinduced Discharge Characteristics of Polyacrylates with Pendant Carbazole Group J. Pol. Sci., Part C: Polymer Letters, vol. 26, pp. 441-446 (1988).
C. I. Simionescu et al., Polymers with Carbazolylalkyl Groups and Their Charge Transfer Complexes with 2,5-cyclohexadien-1,4-diylidenedimalononitrile, Makromol. Chem., 190, pp. 1537-1545 (1989).

*Primary Examiner*—Joseph L. Schofer
*Assistant Examiner*—A. Walker
*Attorney, Agent, or Firm*—Louis G. Xiarhos

[57] ABSTRACT

Ethylenically unsaturated polymerizable acrylic (or methacrylic) monomers having pendant halogenated carbazole moieties, useful for the production of high refractive index polymers, are disclosed. The monomers are useful for the bonding of optical elements in the fabrication of optical devices.

12 Claims, 2 Drawing Sheets

HIGH REFRACTIVE INDEX POLYMERS

BACKGROUND OF THE INVENTION

This invention relates to novel polymerizable monomers for the production of polymers having application in the production of optical devices. More particularly, it relates to certain polymerizable monomers for use in the production of polymers exhibiting high refractive indices.

In the production of optical devices, such as those fabricated from glass or plastic materials or components, design considerations will oftentimes dictate the use of polymeric materials having particular optical properties. In U.S. Pat. No. 4,426,505 (issued Jan. 17, 1984 to R. A. Minns) there is described, for example, the production of certain polyvinyl polymers which combine a relatively high index of refraction with a relatively high Abbe number, so as to provide optical properties which exceed those of the polymers which are used conventionally in the manufacture of plastic lenses.

In the production of optical elements, components and devices, particular performance requirements may dictate the need for polymeric materials which have a high index of refraction. In addition, practical considerations will require that the monomeric precursor materials of such polymers, or the polymers, have melting, softening or other physical properties which permit the polymers to be incorporated into an optical element, component or device. For example, a polymeric material exhibiting a desirably high index of refraction may exhibit softening point or glass transition temperatures which are higher than can be accommodated in the manufacture of an optical element, component or device. Similarly, polymeric materials which can be readily formed or fabricated will oftentimes fail to exhibit the high index of refraction desired for a particular application. It will be appreciated, therefore, that there will be considerable interest in monomers which can be readily polymerized in place to provide high refractive index polymers.

SUMMARY OF THE INVENTION

It has been found that polymers having high refractive indices can be prepared from certain polymerizable monomers of the acrylic (or methacrylic) ester type having pendant halogenated carbazole moieties spaced from the reactive (polymerizable) acrylic or methacrylic ester group by a spacer or linking group. In one of its composition aspects, the present invention provides a polymerizable monomer having the formula:

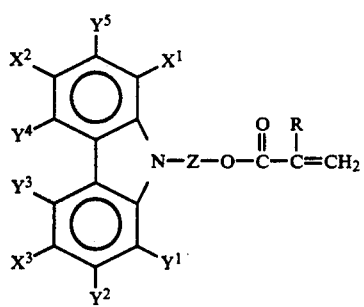

Formula (A-1)

wherein each of $X^1$, $X^2$ and $X^3$ is chlorine, bromine or iodine; each of $Y^1$, $Y^2$, $Y^3$, $Y^4$ and $Y^5$ is hydrogen, chlorine, bromine or iodine; R is hydrogen or methyl; and Z is a linking group

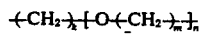

wherein k is an integer of from 1 to 12, m is an integer of from 2 to 4, and n is zero or the integer one or two.

In another of its compositional aspects, the invention provides a polymer comprising repeating units of the formula:

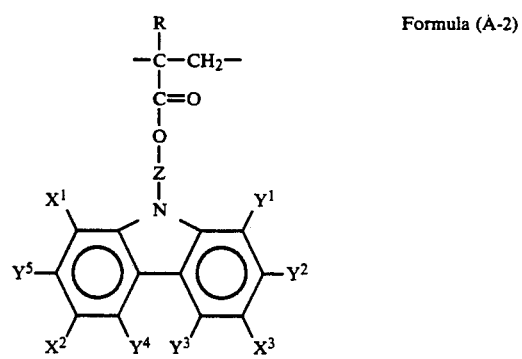

Formula (A-2)

wherein R, Z, $X^1$, $X^2$, $X^3$, $Y^1$, $Y^2$, $Y^3$, $Y^4$ and $Y^5$ have the aforedescribed meanings.

DETAILED DESCRIPTION OF THE INVENTION

Figure 1:
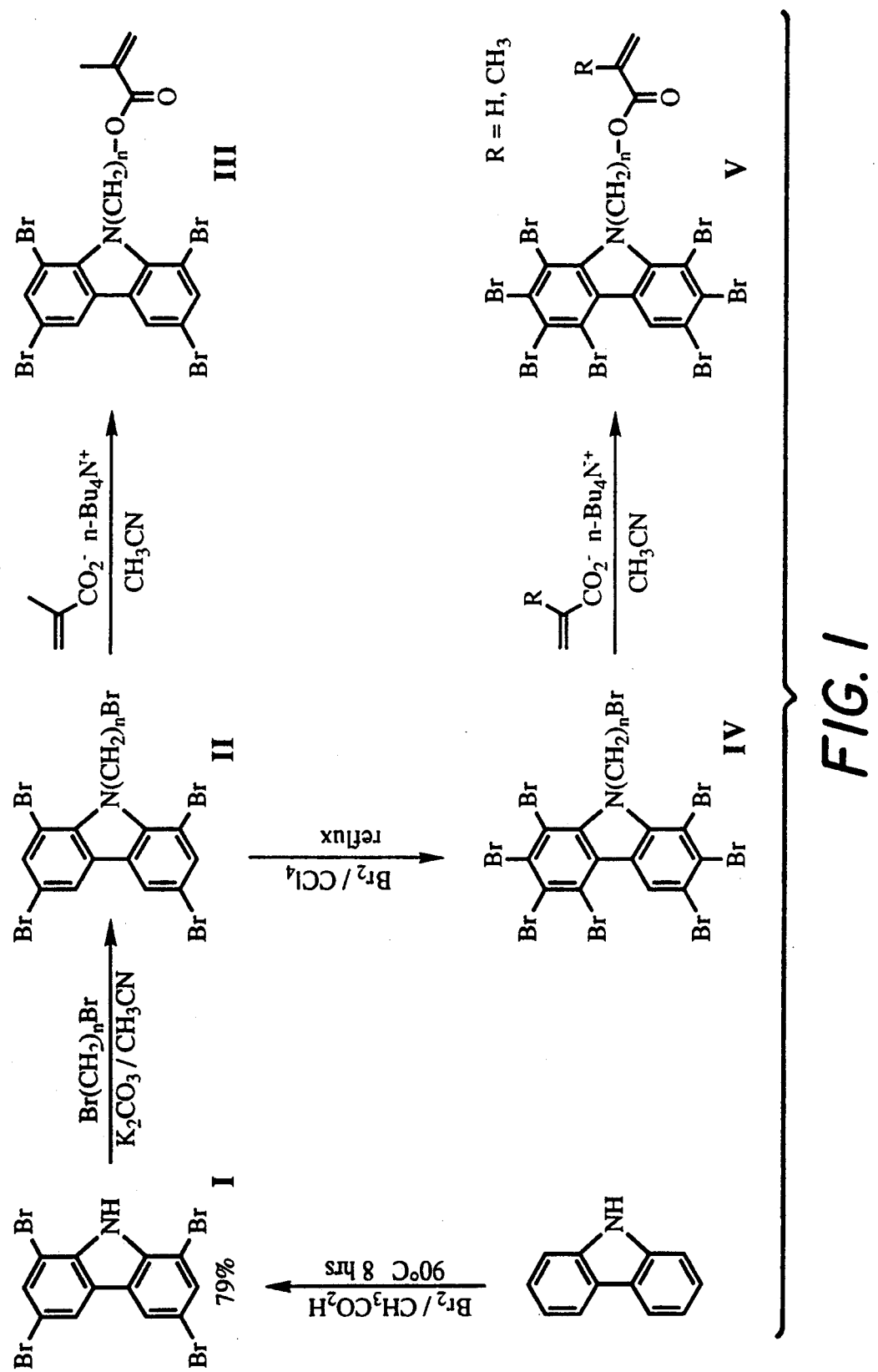
FIG. 1 shows a reaction scheme for the production, starting with carbazole, of certain polymerizable acrylic monomers of the invention having pendant bromine-substituted carbazole moieties.

As mentioned previously, the polymerizable monomers of the invention, represented by Formula (A-1), are useful for the production of polymers which have the repeating units represented by Formula (A-2) and which exhibit high indices of refraction. The refractive indices of homopolymers, for example, are generally in the range of from 1.67 to 1.77. It can be seen from inspection of Formula (A-1) and the meanings set forth in connection therewith, that the polymerizable monomer of the invention comprises an ethylenically unsaturated polymerizable acrylic (or methacrylic) ester group and a pendant halogen-substituted carbazole moiety which is linked to the polymerizable group by a spacer or linking group, Z. The halogen-substituted carbazole moieties include certain halogen groups ($X^1$, $X^2$ and $X^3$) which independently can comprise chlorine, bromine or iodine. It will be seen, thus, that the pendant carbazole nucleus contains at least three halogen substituents. In general, each of $X^1$, $X^2$ and $X^3$ will be the same halogen, for ease in synthetic preparation. These substituent groups need not, however, be the same. Since refractive index will normally vary in the order Cl<Br<I, it will be preferred that the $X^1$, $X^2$ and $X^3$ substituents be bromine or iodine.

Additional positions on the pendant carbazole moiety, represented by $Y^1$, $Y^2$, $Y^3$, $Y^4$ and $Y^5$, can also be halogen, i.e., chlorine, bromine or iodine; or each of $Y^1$, $Y^2$, $Y^3$, $Y^4$ and $Y^5$ can be hydrogen. In general, good results, from the standpoint of providing polymers of high index of refraction, can be obtained where each of $X^1$, $X^2$ and $X^3$ is chlorine, bromine or iodine (preferably, bromine or iodine) and each of the Y groups is hydrogen. Good results are also obtained where each of $X^1$, $X^2$ and $X^3$ is chlorine, bromine or iodine (preferably, bromine or iodine), $Y^1$ is chlorine, bromine or iodine (preferably, bromine or iodine) and each of $Y^2$, $Y^3$, $Y^4$ and $Y^5$ is hydrogen. Refractive indices can be varied with the number and type of halogen substituent and be controlled to meet particular requirements.

Spacer or linking group Z provides an important function in control of the melting temperature of the monomeric compound and of physical, e.g., glass transition, properties of corresponding polymers. Linking group Z, represented by the formula,

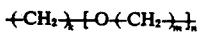

can be an alkylene linking group (where n is zero) or can be an oxygen ether-containing group (where n is an integer one or two). Preferably, for ease in preparation, n will be zero, and k will an integer of from 1 to 12 (e.g., 2 to 6). Alkylene linking groups of from 2 to 6 carbon atoms serve to effectively link the halogenated carbazole moiety to the reactive (polymerizable) ester group of the monomer.

If desired, linking group Z can include oxygen ether atoms, i.e., where n is one or two. Such linking groups can be incorporated into the monomers of the invention by an alkylation procedure, using an $\alpha,\omega$-dibromomonoether or diether. Preferably, m will be 1,2-ethylene and n will be one or two in the case of such ether linking groups, Z.

The nature of linking group Z can influence important properties of polymers prepared from the polymerizable monomers of the invention. In general, a lengthening of the Z linking group will tend to decrease indices of refraction while tending also to lower melting points and glass transition temperatures. It will be appreciated that it will be preferred that spacer group Z comprise a group which allows the monomer to be applied or processed readily in a manufacturing operation and that, therefore, a flexible linking group having, for example, 4 to 6 carbon atoms will be preferred. The index-lowering effect associated with increasing length of the spacer (for desired processability) can be compensated for, in part, by the presence of the halogen substituents on the carbazole moiety. For example, the refractive index of polyvinylcarbazole (no halogen substituents and no spacer) and of poly[4-(1,3,6,8-tetrabromo-9-carbazolyl)-1-butyl methacrylate] is in each case 1.68.

Good results from the standpoints of providing low monomer melting points (for improved processing, particularly in the application of monomer to optical components or devices for processing in place) and high indices of refraction of the resulting polymers can be obtained by using a mixture of monomer compounds having different spacer groups. The mixtures melt at lower temperatures than the individual compounds. In the case of heptabromocarbazole methacrylates, a preferred mixture is a ternary mixture composed of equal weights of such compounds having butylene, pentylene and hexylene linking groups. Although the melting temperature of this composition is very broad (and the composition is a soft and taffy-like solid at room temperature), it converts completely to an isotropic liquid at 50° C., provides a high index of refraction (1.72) and can be used as an adhesive for the bonding of optical elements or components.

The polymerizable monomer of Formula (A-1) can be an acrylic or methacrylic ester depending upon whether R is hydrogen or methyl. In general, the acrylates will provide polymers of lower glass transition temperature than the corresponding methacrylates.

The polymerizable monomers of Formula (A-1) can be prepared by resort to known organic preparative routes. The monomers can be prepared from carbazole using conventional halogenation, alkylation and esterification steps. The synthesis of unsubstituted carbazole acrylates is known and details of the preparation thereof are reported by Chau-Jin Hu, et al., J. Polym. Sci., Polym. Lett., 26, 441 (1988) and by C. I. Simionescu, et al., in Makromol., Chem., 190, 1537 (1989). In the production of the substituted carbazolecontaining monomers of the invention, the inexpensive and readily available compound, carbazole, can be halogenated (preferably, brominated or iodinated) and then alkylated at the nitrogen atom thereof by reaction with a difunctional compound of the formula

where Hal represents halogen (e.g., bromine). The resulting alkylated compound can then be esterified by reaction, in known manner, with a tetraalkyl ammonium acrylate (or methacrylate).

In FIG. 1 is shown a reaction scheme for the production of certain preferred acrylate (and methacrylate) monomers of the invention having pendant bromine-substituted carbazole moieties. The reaction scheme of FIG. 1 is intended as being illustrative and is not intended to be limited to the particulars illustrated therein. In FIG. 1, is shown the reaction of carbazole with bromine in acetic acid (at 90° C. for 8 hours) for production of the tetrabrominated carbazole, I. Alternatively, iodination can be conducted similarly under mild conditions with isolation, for example, of the triiodo compound, VI, shown in FIG. 2.

The tetrabromo compound (I) shown in FIG. 1 can be alkylated, as previously mentioned, for attachment of linking (spacer) group Z, using known methodology. As shown in FIG. 1, this can be accomplished by reaction with a large excess of, for example, $\alpha,\omega$-dibromoalkane and potassium carbonate in refluxing acetonitrile. This straightforward reaction provides a high yield of the desired alkylated product, II, shown in FIG. 1. In like manner, the alkylated iodine-substituted carbazole compound, VII, can be prepared, as in shown in FIG. 2.

Figure 2:
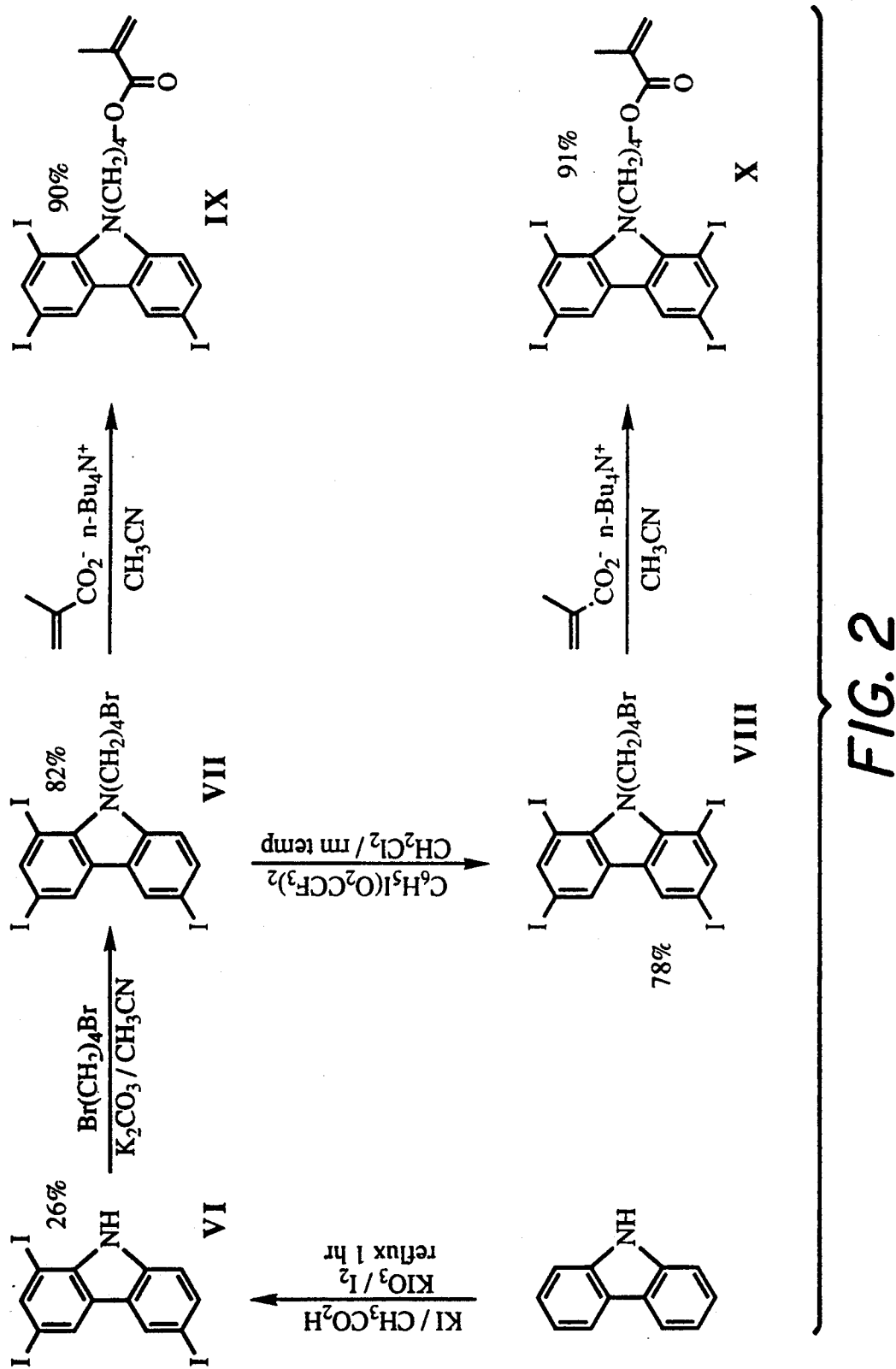
FIG. 2 shows a reaction scheme for the production, starting with carbazole, of certain polymerizable acrylic monomers of the invention having pendant iodine-substituted carbazole moieties.

If desired, higher levels of bromination of the brominated rings of compound II can be achieved by reaction with equal volumes of bromine and tetrachloromethane under reflux, to yield the highly brominated compound shown as compound IV in FIG. 1. In the case of bromination of compound II, only one of the aromatic rings of carbazole could be perbrominated. Bromine could be added to the second ring only at the C-7 position; the C-5 position was completely unreactive as the likely result of steric hindrance by the bromine atom on the C-4 position of the first ring. In like manner, and as shown in FIG. 2, further iodination of an iodine-substituted carbazole (VII) can be effected. Iodination of the ring of compound VII can be accomplished with iodine and [bis(trifluoroacetoxy)iodo]benzene for several days at room temperature to yield compound VIII, shown in FIG. 2. Attempts at higher iodination by this route were not successful, probably because of steric effects.

The desired polymerizable monomer of the invention can be provided in high yield via an esterification reaction, whereby the N-(ω-bromoalkyl) halogenated carbazole (e.g., compound II or VII in FIGS. 1 or 2, respectively) is reacted with the tetrabutylammonium salt of the desired acid anion. In the bromocarbazole series, the yields of III and V ranged from 66–91%; for the two iodinated methacrylates, IX and X, the yields were 90 and 91%.

The polymerizable monomers of Formula (A-1) can be polymerized, for example, by thermal, bulk polymerization or by conventional free-radical solution polymerization methods based upon free-radical initiators such as azobisisobutyronitrile and azobis-$\alpha,\gamma$-dimethylvaleronitrile. Such methods are known in the art and the desired polymers can be isolated by evaporation of the polymerization solvent or, by precipitation into a non-solvent for the polymer.

Polymerization of the monomer can be performed readily by melting the monomer (or a mixture thereof) between glass circles on a Fisher-Johns melting point apparatus and maintaining the liquid at a temperature above its melting point for several minutes. The glass circles adhere together as the polymer is formed, resulting in an optically clear and colorless sandwich. For example, the compound IIIb shown in Table 1 hereinafter, when maintained for several minutes at 170° C. in such an apparatus, yields the corresponding homopolymer which softens at approximately 200° C. and can be made to flow at 250° C. without discoloration. Upon cooling, the glass elements can be pried apart (with a razor blade) or dissolved in hydrofluoric acid to separated the brittle polymer. Similarly, a low-melting blend (mp<50° C.) of three heptabromo monomers V (with n=4,5 and 6) was prepared by dissolving 20 mg each of Vb, Vc and Vd (described in Table 1) in dichloromethane, filtering the solution and evaporating the solvent in a stream of nitrogen. Application of a vacuum to remove final traces of solvent yielded a taffy-like foam. A sample thereof placed between two glass circles on a Fisher-Johns melting point apparatus melted below 50° C. to a clear liquid and polymerized at approximately 100° C. to a clear film.

The polymerizable monomers of the invention can be used in the production of optical elements, components and devices particularly by polymerization in place. For example, in U.S. Pat. No. 4,446,305 (issued May 1, 1984 to H. G. Rogers, et al.) there are described optical devices based upon highly birefringent rod-like polymers, including an optical beam splitter having a film of birefringent polymer between a pair of prismatic elements. A mixture of polymerizable monomers of the invention can be utilized as an adhesive for the elements of such an optical device and can be polymerized in place. The mixture can be liquified and polymerized between the elements thereof to provide a colorless, non-birefringent, amorphous optical binding agent exhibiting a high refractive index, e.g., in the range of 1.67 to 1.77.

The polymerizable monomers of the invention are characterized by properties especially suited for optical applications where a high index polymer is required. Typically, a material suited for such applications (1) should be a liquid or a low-melting solid near room temperature; (2) must not dissolve or swell the polymer film or other element or component of the fabricated device; and (3) must polymerize rapidly by thermal or photochemical initiation.

Polymers produced from the monomers must (1) bond polymer films to glass or other polymer films; (2) be optically transparent, i.e., colorless and nonscattering; (3) not be too brittle; and (4) have a high index of refraction, e.g., >1.67.

Monomers and polymers which provide the aforementioned advantages and meet the aforementioned requirements are provided by the present invention. Further illustration of the invention is set forth in the following examples which are intended as illustrative and not limitative of the invention. All parts and proportions, except where otherwise noted, are by weight. Molecular structure was confirmed in each Example by NMR and mass spectral analyses.

EXAMPLE 1

Part A—Preparation of 1,2,6,8-Tetrabromocarbazole (FIG. 1. Compound I)

Into a 250-ml, three-necked, round-bottomed flask equipped with an oil bath, a magnetic stirrer, a thermometer, an addition funnel, and a condenser topped by a calcium chloride drying tub=leading to a water trap for evolved HBr were placed 3.4 g (0.02 mole) carbazole and 50 ml glacial acetic acid. With stirring at room temperature, a solution of 4.5 ml bromine in 50 ml acetic acid was run in, then the oil bath was heated to 90° and the mixture was stirred for 8 hours. After standing overnight at room temperature, the product was collected by filtration and recrystallized from toluene/acetic acid to yield 7.6 g (79%) of light yellow crystals, mp 228°–231° C. (mp 233°–5° C. from literature, J. Pielichowski and J. Kyziol, Monarshefte Chemie, 105, 1306 (1974).

Part B—Preparation of 9-(4-bromobutyl)-1,3,6,8-tetrabromocarbazole (FIG. 1, Compound II. n=4)

Into a 100-ml, three-necked, round-bottomed flask equipped with an oil bath, a magnetic stirrer, a thermometer, and a condenser connected to a nitrogen bubbler were placed 1.0 g I, 5 ml (20 equiv) 1,4-dibromobutane, 3 g (10 equiv) powdered anhydrous potassium carbonate, and 20 ml anhydrous acetonitrile. The mixture was stirred under reflux with the oil bath at 100° C. for 18 hours. Most of the acetonitrile was then distilled, water and dichloromethane were added, and the two phases were separated. The aqueous phase was extracted twice with dichloromethane, and the combined organic phase was dried over anhydrous sodium sulfate and filtered through a pad of Celite ® to give a light-yellow clear solution. Dichloromethane and most of the excess 1,4-dibromobutane were evaporated on a steam bath in a stream of nitrogen. The resulting oil was dissolved in 100 ml boiling dichloromethane, and methanol was added until crystals appeared. After cooling in an ice-water bath, the light yellow crystals were filtered and dried to yield 1.02 g (80%); mp 142°–4° C.

The following homologues of the compound of Part B of this Example were similarly prepared:
n=2, 92% yield, mp 191°–4° C.
n=3, 93% yield, mp 157°–9° C.
n=5, 93% yield, mp 136°–8° C.
n=6, 90% yield, mp 122°–3° C.

Part C—Preparation of Compound IIIb, 4-(1,3,6,8-tetrabromo-9-carbazolyl)-1-butyl methacrylate (FIG. 1, Compound III, n=4).

A solution of tetrabutylammonium methacrylate was prepared in a 50-ml round-bottomed flask by titrating 0.1 ml methacrylic acid in 10 ml methanol with approximately 1.2 ml of a 1M solution of tetrabutylammonium hydroxide in methanol until the solution was just basic to wet pH paper. The solution was acidified with several drops of methacrylic acid, and the solvents were removed on a rotary evaporator at 30° C. Acetonitrile was then added and evaporated to remove remaining water and methanol. The resulting oil was dissolved in 10 ml acetonitrile, and 682 mg 9-(4-bromobutyl)-1,3,6,8-tetrabromocarbazole along with 10 ml benzene were added. The mixture was warmed briefly to effect solution, and the resulting solution was stirred overnight at room temperature under nitrogen. Solvents were then evaporated with the temperature maintained below 40° C., water was added, and the mixture was extracted with benzene. The organic phase was dried and evaporated, and the crude product was purified by flash chromatography on silica gel with 1:1 dichloromethane/hexanes to yield 594 mg (86%) white crystals; mp 155°–156.5° C.

The following homologues of the compound (IIIb) of Part C of this Example were similarly prepared:
IIIa, n=3, mp 177°–8° C.
IIIc, n=5, 72% yield, mp 146°–8° C.
IIId, n=6, 94% yield, mp 124°–6° C.

EXAMPLE 2

Part A—Preparation of 9-(6-bromohexyl)-1,2,3,4,6,7,8-Heptabromocarbazole (FIG. 1, Compound IV, n=6)

Into a 250-ml round-bottomed flask equipped with an oil bath, a magnetic stirrer, and a condenser topped by a calcium chloride drying tube leading to a water trap for evolved HBr were placed 5.0 g (7.74 mmol) 9-(6-bromohexyl)-1,3,6,8-tetrabromocarbazole, 50 ml bromine, and 50 ml tetrachloromethane. The solution was stirred overnight under reflux. Excess bromine and tetrachloromethane were then recovered by distillation for use in another run, and the solid was blown dry in a stream of nitrogen. Recrystallization from carbon disulfide/ethanol yielded 6.23 g (91%) of a white solid; mp 161°–2° C. The following homologues of the compound of Part A of this Example were similarly prepared:
n=4, mp 189°–91° C.
n=5, 84% yield, mp 165°–7° C.

Part B—Preparation of γ-(1,2,3,4,6.7,8-heptabromo-9-carbazolyl)-α-alkyl (meth)acrylates (FIG. 1, Compound V)

These monomers (Compounds Va, Vb, Vc and Vd) were prepared from the alkyl bromides by a procedure analogous to that described in EXAMPLE 1, Part C, for the preparation of 4-(1,3,6,8-tetrabromo-9-carbazolyl)-1-butyl methacrylate above. The structures (V) were confirmed by NMR and mass spectral analyses.
Va, n=4, R=H, 66% yield, mp 164°–6° C.
Vb, n=4 R=Me, 77% yield, mp 170°–2° C.
Vc, n=5, R=Me, 91% yield, mp 145°–6° C.
Vd, n=6, R=Me, 88% yield, mp 120°–1° C.

EXAMPLE 3

Part A—Preparation of 1,3,6-Triiodocarbazole (FIG. 2, Compound VI)

The above-named compound was prepared by the following procedure, a modification of the preparation described by S. H. Tucker, in J. Chem. Soc., 1926, 546.

Into a 250-ml, three-necked, round-bottomed flask equipped with a heating mantle, a magnetic stirrer, and a condenser were placed 8.35 g (0.05 mole) carbazole, 11 g (0.066 mole) potassium iodide, and 125 ml glacial acetic acid. The mixture was heated to reflux with stirring, the resulting solution was cooled slightly, and 16 g (0.075 mole) potassium iodate was cautiously added with stirring. After stirring under reflux for 15 minutes, the iodine color faded. 5 g (0.02 mole) iodine was added and the reaction mixture was stirred under reflux for one hour. It was then poured into an aqueous solution of sodium bisulfite, and the precipitated solid was collected by filtration and extracted with acetone in a Sohlet extractor. Fractional crystallization from acetone yielded two products with $R_f$ values of 0.33 and 0.64 as determined by thin layer chromatographic analysis on silica gel with 20% dichloromethane in hexanes. The lower $R_f$ product was an off-white solid, 7.0 g (26%); mp 228°–238° C.

A sample that was purified by flash chromatography on silica gel with carbon disulfide followed by recrystallization from carbon disulfide/hexanes had a melting point of 237°–8° C.

Part B—Preparation of 9-(4-bromobutyl)-1,3,6-triiodocarbazole (FIG. 2, Compound VII)

This compound was prepared from Compound VI of Part A of this Example by an alkylation procedure analogous to that described for the preparation of II. Off-white crystals were obtained in 82% yield; mp 143°–5° C.

Part C—Preparation of 4-(1,3,6-triiodo-9-carbazolyl)-1-butyl methacrylate (FIG. 2, Compound IX)

The above-named compound was prepared from the alkyl bromide using a procedure analogous to that described in EXAMPLE 1, Part C for the production of Compound III, with the following results.
IX, 90% yield, mp 157°–9° C.

EXAMPLE 4

Part A—Preparation of 9-(4-bromobutyl)-1,3,6,8-tetraiodocarbazole (FIG. 2, Compound VIII)

Into a 100 ml round-bottomed flask equipped with a magnetic stirrer were added 1.0 g (1.47 mmol) VII, 200 mg (0.79 mmol) iodine, 350 mg (0.81 mmol) [bis(trifluoroacetoxy)iodo]-benzene, and 50 ml dichloromethane. After stirring the dark purple solution at room temperature for five hours, a white solid began to precipitate. Stirring was continued at room temperature for two days, then the mixture was allowed to stand at room temperature for an additional four days. The white solid was collected by filtration and washed with a small volume of dichloromethane to yield 930 mg (78%) of product; mp 211°–4° C.

Part B—Preparation of 4-(1,3,6,8-tetraiodo-9-carbazolyl)-1-butyl methacrylate (FIG. 2, Compound X)

The above-named compound was prepared from the alkyl bromide using a procedure analogous to that described in EXAMPLE 1, Part C for the production of Compound III, with the following results.
X, 91% yield, mp 157°–9° C.

EXAMPLE 5

This Example illustrates the thermal, bulk polymerization of 4-(1,3,6,8-tetrabromo-9-carbazolyl)-1-butyl methacrylate, i.e., the Compound (IIIb) of EXAMPLE 1, Part C.

Into a 10-ml, round-bottomed flask was placed 280 mg of Compound IIIb. The flask was evacuated continuously with a mechanical vacuum pump and heated at 160° C. for two hours. The resulting polymer was dissolved in 3 ml 1-chloronaphthalene with stirring at 150° C., then the viscous solution was filtered. The polymer was precipitated into 70 ml dichloromethane, filtered, washed thrice with dichloromethane and dried to yield 207 mg (74%) white polymer; $\eta_{inh}=0.68$ dl/g (1-chloronaphthalene), Tg=160° C. as determined by differential scanning calorimetry, $n_d=1.68$ as determined by microscopy using Becke line analysis.

Monomers of the invention can also be polymerized by melting them between two glass circles on a Fisher-Johns melting point apparatus and holding the liquid at a temperature above its melting point for several minutes. The glass circles lock together as the polymer is formed, resulting in an optically clear and colorless sandwich. For example, maintaining Compound IIIb at 170° C. for several minutes yields the polymer which softens at approximately 200° C., and can be made to flow at 250° C. without discoloration. Upon cooling, the glass can be pried apart with a razor blade or dissolved in hydrofluoric acid to separate the brittle polymer.

EXAMPLE 6

A low-melting blend (mp<50° C.) of the three heptabromo monomers V with n=4, 5, and 6 was prepared by dissolving 20 mg each of compounds Vb, Vc and Vd in 2 ml dichloromethane, filtering the solution, and evaporating the solvent in a stream of nitrogen. Application of a vacuum to remove final traces of solvent yielded a taffy-like foam. A sample that was placed between two circles on a Fisher-Johns melting point apparatus melted below 50° C. to a clear liquid and polymerized at approximately 100° C. to a clear film.

Thermal and optical properties of monomers and polymers described in EXAMPLES 1 to 5 and conforming to the following formula are set forth in the following TABLE 1.

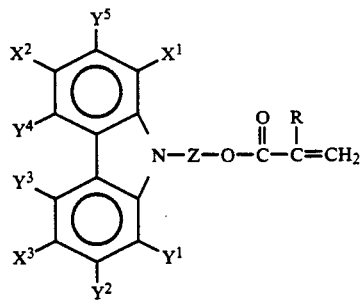

wherein each of $X^1$, $X^2$ and $X^3$ is chlorine, bromine or iodine; each of $Y^1$, $Y^2$, $Y^3$, $Y^4$, and $Y^5$ is hydrogen, chlorine, bromine or iodine; R is hydrogen or methyl; and Z is a linking group

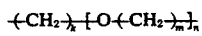

wherein k is an integer of from 1 to 12, m is an integer of from 2 to 4, and n is zero or the integer one or two.

2. The polymerizable monomer of claim 1 wherein each of $X^1$, $X^2$ and $X^3$ is bromine or iodine.

3. The polymerizable monomer of claim 2 wherein $Y^1$ is bromine or iodine.

4. The polymerizable monomer of claim 2 wherein $Y^3$ is hydrogen.

5. The polymerizable monomer of claim 2 wherein each of $Y^2$, $Y^4$, and $Y^5$ is hydrogen or bromine.

6. The polymerizable monomer of claim 2 wherein each of $X^1$, $X^2$ and $X^3$ is bromine.

7. The polymerizable monomer of claim 6 wherein $Y^1$ is bromine.

8. The polymerizable monomer of claim 7 wherein $Y^3$ is hydrogen and $Y^1$, $Y^2$, $Y^4$, and $Y^5$ are each bromine.

9. The polymerizable monomer of claim 2 wherein each of $X^1$, $X^2$ and $X^3$ is iodine.

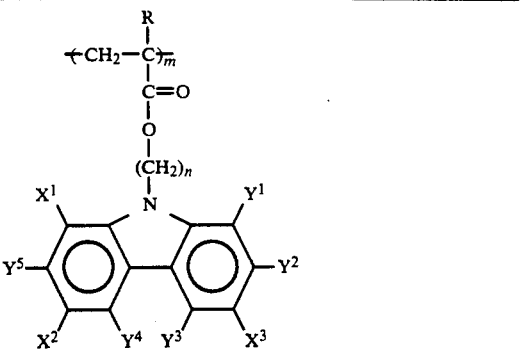

| $X^1, X^2, X^3$ | $Y^1$ | $Y^3$ | $Y^2, Y^4, Y^5$ | n | R | monomer No. | mp | $\eta_{inh}$ | $T_g$ | $T_{dec}$ | $n_D$ |
|---|---|---|---|---|---|---|---|---|---|---|---|
| Br | Br | H | H | 3 | Me | IIIa | 177–8° | — | — | — | — |
| Br | Br | H | H | 4 | Me | IIIb | 155–7° | 0.68 | 160° | 335° | 1.68 |
| Br | Br | H | H | 5 | Me | IIIc | 146–8° | 0.27 | 132° | 387° | — |
| Br | Br | H | H | 6 | Me | IIId | 124–6° | 0.28 | 112° | 400° | 1.67 |
| Br | Br | H | Br | 4 | H | Va | 164–6° | 0.07 | 176° | — | — |
| Br | Br | H | Br | 4 | Me | Vb | 170–2° | 0.17 | 198° | 382° | 1.74 |
| Br | Br | H | Br | 5 | Me | Vc | 145–6° | 0.21 | 185° | 385° | — |
| Br | Br | H | Br | 6 | Me | Vd | 120–1° | 0.10 | 163° | 377° | 1.72 |
| Br | Br | H | Br | 4, 5, 6 | Me | Ve | <50° | 0.19 | 175° | 390° | 1.72 |
| I | H | H | H | 4 | Me | IX | 157–9° | 0.10 | — | — | 1.74 |
| I | I | H | H | 4 | Me | X | −210° | — | — | — | 1.77 |

10. The polymerizable monomer of claim 9 wherein each of $Y^1$, $Y^2$, $Y^3$, $Y^4$, and $Y^5$ are is hydrogen.

11. The polymerizable monomer of claim 9 wherein $Y^1$ is iodine and each of $Y^2$, $Y^3$, $Y^4$, and $Y^5$ is iodine.

12. The polymerizable monomer of claim 1 wherein n is zero and k is an integer from 2 to 6.

What is claimed is:

1. A polymerizable monomer having the formula

* * * * *